(12) United States Patent
Keeling

(10) Patent No.: US 12,082,991 B2
(45) Date of Patent: Sep. 10, 2024

(54) THREE-DIMENSIONAL DENTAL SCANNING SYSTEM AND METHOD OF SCANNING

(71) Applicant: University of Leeds, Leeds (GB)

(72) Inventor: Andrew James Keeling, Leeds (GB)

(73) Assignee: University of Leeds, Leeds (GB)

( * ) Notice: Subject to any disclaimer, the term of this patent is extended or adjusted under 35 U.S.C. 154(b) by 145 days.

(21) Appl. No.: 17/761,349

(22) PCT Filed: Sep. 17, 2020

(86) PCT No.: PCT/GB2020/052255
§ 371 (c)(1),
(2) Date: Mar. 17, 2022

(87) PCT Pub. No.: WO2021/053338
PCT Pub. Date: Mar. 25, 2021

(65) Prior Publication Data
US 2022/0346920 A1    Nov. 3, 2022

(30) Foreign Application Priority Data

Sep. 18, 2019   (GB) ..................... 1913469

(51) Int. Cl.
*G06T 7/579* (2017.01)
*A61B 5/00* (2006.01)
(Continued)

(52) U.S. Cl.
CPC ............ *A61C 9/006* (2013.01); *A61B 5/0088* (2013.01); *G06T 7/0012* (2013.01); *G06T 7/521* (2017.01);
(Continued)

(58) Field of Classification Search
CPC . G06T 2207/30036; G06T 2207/10028; G06T 2210/36; A61C 9/0053; A61C 9/006; A61B 5/0088
See application file for complete search history.

(56) References Cited

U.S. PATENT DOCUMENTS

| 5,078,599 A | 1/1992 | Eenboom et al. |
| 8,821,158 B1 | 9/2014 | Hultgren |
| (Continued) | | |

FOREIGN PATENT DOCUMENTS

| DE | 4301538 A1 | 7/1994 | |
| DE | 19651909 A1 * | 6/1998 | ......... A61C 13/0004 |
| (Continued) | | | |

OTHER PUBLICATIONS

Richard Hartley et. al., "Multipe View Geometry in Computer Vision." Second Edition (2003). Cambridge University Press.

*Primary Examiner* — Diane M Wills
(74) *Attorney, Agent, or Firm* — Downs Rachlin Martin PLLC

(57) ABSTRACT

A three-dimensional (3D) dental scanning system (1) for scanning a dental object (D) includes a scanning surface (124a) to support the dental object (D); a scanning section (130) to capture a 3D scan of the dental object (D); a motion section (120) to move the scanning surface (124a) and scanning section (130) relative to each other in five axes of motion, whilst retaining the scanning surface (124a) in a substantially horizontal plane, and a control unit (140) configured to control the motion section (120) and the scanning section (130) to obtain a 3D scan of the dental object (D).

14 Claims, 13 Drawing Sheets

(51) Int. Cl.
  *A61C 9/00*    (2006.01)
  *G06T 7/00*    (2017.01)
  *G06T 7/521*   (2017.01)
(52) U.S. Cl.
  CPC .... *G06T 7/579* (2017.01); *G06T 2207/10028* (2013.01); *G06T 2207/30036* (2013.01); *G06T 2207/30244* (2013.01); *G06T 2210/36* (2013.01)

(56) References Cited

U.S. PATENT DOCUMENTS

| | | | |
|---|---|---|---|
| 2010/0134598 A1* | 6/2010 | St-Pierre | G01B 11/2513 |
| | | | 348/47 |
| 2014/0051037 A1 | 2/2014 | Fisker | |
| 2014/0368614 A1* | 12/2014 | Imai | G01B 21/047 |
| | | | 348/47 |
| 2016/0161250 A1* | 6/2016 | Nakamura | G01B 11/2513 |
| | | | 356/610 |
| 2019/0164353 A1 | 5/2019 | Yancey et al. | |
| 2019/0378344 A1 | 12/2019 | Long et al. | |

FOREIGN PATENT DOCUMENTS

| | | | | |
|---|---|---|---|---|
| DE | 102004021910 A1 * | 2/2006 | | A61C 13/0004 |
| DE | 102013203312 A1 | 8/2014 | | |
| EP | 2312268 A1 | 4/2011 | | |
| EP | 3195826 A1 | 7/2017 | | |

\* cited by examiner

THREE-DIMENSIONAL DENTAL SCANNING SYSTEM AND METHOD OF SCANNING

FIELD

The present invention relates to a three-dimensional dental scanning system for scanning a dental object, and methods of scanning a dental object.

BACKGROUND

For a wide variety of applications, it is desirable to accurately capture a three-dimensional (3D) model of a patient's intra-oral structures (i.e. the teeth and gums). For example, such 3D models find utility in the production of dental prostheses and implants, wherein laboratories will use computer-aided design (CAD) software to design such prostheses based on the 3D models, and then subsequently manufacture the prosthesis or implant. Accordingly, it is highly desirable that the captured 3D model accurately reflects the patient's intra-oral structures, so that any manufactured prosthesis or implant properly fits the patient.

In a typical workflow, a dentist will take a dental impression of the patient's intra-oral structures in the dental surgery. This is accomplished by placing an impression material in the patient's mouth, whereupon the patient bites the impression material and deforms it, producing a negative imprint of the intra-oral structures. The impression may then be posted to a dental laboratory. The dental laboratory will cast a model from the impression. The cast model may then be clamped into a dental scanner, whereupon the cast model is moved relative to a scanning head in order to capture a model.

Difficulties arise in that the dental impressions may deform in transit or storage, for example due to changes in temperature, thereby compromising the accuracy of the resulting cast model and captured 3D model. In addition, the process of casting the model may cause deformation of the impression.

Further difficulties arise in that 3D scanners tend to use pre-programmed motion paths in an attempt to fully cover the scanned object. However, regions of the object may be missed, and the operator must manually add scans to cover the missing regions. This may require training to be carried out with relative accuracy.

In another typical workflow, an intra-oral 3D scanner is placed in the mouth of the patient in the dental surgery and moved around the patient's mouth to capture a 3D model. However, such devices are prohibitively expensive, and may lack accuracy.

It is an aim of the disclosure to overcome the above-mentioned difficulties, and any other difficulties that may be apparent to the skilled reader from the description herein. It is a further aim of the disclosure to provide a cost-effective and accurate 3D scanner for scanning dental objects such as dental impressions which does not require specialist skills or training to operate.

SUMMARY

According to the present invention there is provided an apparatus and method as set forth in the appended claims. Other features of the invention will be apparent from the dependent claims, and the description which follows.

According to a first aspect of the disclosure there is provided a three-dimensional (3D) dental scanning system for scanning a dental object, comprising:

a scanning surface configured to support the dental object;
a scanning section configured to capture a 3D scan of the dental object; and
a motion section configured to move the scanning surface and scanning section relative to each other in five axes of motion, whilst retaining the scanning surface in a substantially horizontal plane The system may comprise a control unit configured to control the motion section and the scanning section to obtain a 3D scan of the dental object.

The control unit may be configured to:
identify a region of a point cloud of the dental object captured at a level of detail below a predetermined detail level;
identify a scanning position for capturing the identified region; and
control the motion section to move the scanning surface and scanning section to scan the identified region.

The control unit may be configured to surface the point cloud to produce a 3D model, and uniformly sample the surfaced model to generate a uniformly sampled point cloud. The control unit may be configured to: identify a closest point in the point cloud to each point in the uniformly sampled point cloud, and flag the point in the uniformly sampled point cloud as below the predetermined detail level in response to a distance between the point in the uniformly sampled point cloud and the identified closest point exceeding a threshold distance.

The control unit may be configured to determine an optimal viewing position for each flagged point. The optimal viewing position may be based on an optimal focal distance of the scanning section. The optimal view position may be based on a normal line extending from the flagged point. The control unit may be configured to verify each optimal viewing position to determine that the flagged point will not be occluded when viewed from the scanning section.

The control unit may be configured to determine that the optimal viewing position is occluded, and adjust the optimal viewing position to reach an unoccluded position. The optimal viewing position may be adjusted by adjusting the angle of the normal line. The optimal viewing position may be adjusted by adjusting the position along the normal line. The optimal viewing position may be iteratively adjusted until the unoccluded position is reached. The control unit may be configured to rank each optimal viewing position according to the number of flagged points visible therefrom.

The control unit may be configured to iteratively identify a region of a point cloud of the dental object captured at a level of detail below a predetermined detail level; identify a scanning position for capturing the identified region; and control the motion section to move the scanning surface and scanning section to scan the identified region of the second aspect may be carried out iteratively. Accordingly, the point cloud of the dental object may be a point cloud obtained by a previous iteration of the steps defined hereinabove. The point cloud of the dental object may be an initial point cloud and may be obtained by a pre-programmed scan sequence.

The motion section may comprise a plurality of actuators configured to move the scanning surface and scanning section relative to each other. The control unit may be configured to control the plurality of actuators.

The five axes of motion may comprise translation, preferably of the scanning surface, in a first horizontal direction, which may be an X direction. The motion section may comprise a first linear actuator configured to translate the scanning surface in the X direction.

The five axes of motion may comprise translation, preferably of the scanning surface, in a second horizontal direction. The second horizontal direction may be perpendicular to the first horizontal direction, and may be a Y direction. The motion section may comprise a second linear actuator configured to translate the scanning surface in the Y direction. The first linear actuator may be configured to translate the second linear actuator in the X direction.

The five axes of motion may comprise translation, preferably of the scanning section, in a vertical direction. The vertical direction may be a Z direction. The motion section may comprise a vertical linear actuator configured to translate the scanning section in the Z direction. The scanning section may be movable to a position in the vertical direction that is in substantially the same horizontal plane as the dental object and/or scanning surface. A lower end of the vertical linear actuator may extend to a position at, or below, the same horizontal plane as the dental object and/or scanning surface.

The five axes of motion may comprise rotation of the scanning surface. The rotation of the scanning surface may be about a substantially vertical axis perpendicular to a plane of the scanning surface. The motion section may comprise a rotary actuator to rotate the scanning surface.

The five axes of motion may comprise tilt of the scanning section. The motion section may comprise a tilt actuator is configured to tilt the scanning section. The tilt actuator may be configured to alter the pitch of the scanning section. The tilt actuator may be configured to tilt the scanning section about a substantially horizontal axis. The substantially horizontal axis may be disposed below the scanning section.

The motion section may be configured to permit freedom of movement of the scanning section with respect to a centre of the scanning surface. The plurality of actuators may be each independently actuated. The scanning surface and the scanning section may not be retained in a fixed relationship, suitably a relationship in which the centre of the scanning surface is retained in the centre of the view of the scanning section.

The scanning section may comprise a projector configured to project a structured light pattern onto the dental object. The scanning section may comprise a camera, preferably two cameras. The cameras may be disposed on the same horizontal plane.

The scanning section may comprise a projector configured to project a structured light pattern onto the dental object. The scanning section may comprise a camera, preferably two cameras. A first of the two cameras and the projector may be connected by a first notional line. A second of the two cameras and the projector may be connected by a second notional line. The first notional line and second notional line may be non-colinear. The first notional line and second notional line may be orthogonal. A first of the two cameras and the projector may be are arranged in the same horizontal plane. A second of the two cameras and the projector may be arranged in the same vertical plane. The two cameras and the projector may be arranged in a notional "L"-shape, with the projector at the vertex of the "L".

The scanning section may be configured to operate in a first mode in which the first camera and the projector are activated. The first camera and the projector may form a stereo pair with a first baseline extending therebetween. In the first mode, the projector may project structured light patterns that are orthogonal to the first baseline. The first mode may be referred to herein as a horizontal mode. The first baseline may be a horizontal baseline.

The scanning section may be configured to operate in a second mode in which the second camera and the projector are activated. The second camera and the projector may form a stereo pair with a second baseline extending therebetween. In the second mode, the projector may project structured light patterns that are orthogonal to the second baseline. The second mode may be referred to herein as a vertical mode. The second baseline may be a vertical baseline.

The scanning section may be configured to operate in a third mode, in which the first camera, the second camera and the projector are activated. The first and second camera may form a stereo pair with a third baseline extending therebetween. In the third mode, the projector may project structured light patterns that are orthogonal to the third baseline. The third mode may be referred to herein as a diagonal mode. The second baseline may be a diagonal baseline The scanning section may be configured to operate in a trifocal mode, in which the first camera, the second camera and the projector are activated, and each of the first camera, the second camera and the projector form an optic centre. The system may be configured to determine a trifocal tensor in the trifocal mode.

The scanning section may be selectively operable in the horizontal mode and the vertical mode.

The scanning apparatus may comprise an enclosure comprising the scanning surface, the scanning section and the motion section.

The scanning surface may be a substantially planar surface. The scanning system may not comprise securing means for securing the dental object to the scanning surface.

The scanning surface may comprise a high-friction surface to retain the dental object in position during motion of the scanning surface.

In some examples, elements of the system or parts thereof may be disposed remotely from one another, and connected by a suitable communication medium. For example, the elements or parts may be connected via network connection. The network connection may comprise one or more of a local area network (LAN), wide area network (WAN), leased lines or the Internet. The network connection may comprise wired and/or wireless links. In other examples the elements may be linked by a wired communication protocol, such as a USB link or FireWire® link.

The system may comprise a scanning apparatus and a controlling device operable to control the scanning apparatus. The scanning apparatus may comprise the scanning surface, scanning section and motion section.

According to a second aspect of the disclosure there is provided a three-dimensional (3D) scanning method, comprising using the 3D dental scanning system as defined in the first aspect to capture a 3D scan of a dental object.

The 3D scanning method may comprise:
identifying a region of a point cloud of the dental object captured at a level of detail below a predetermined detail level;
identifying a scanning position for capturing the identified region; and
controlling the motion section to move the scanning surface and scanning section to scan the identified region.

The method may comprise surfacing the point cloud to produce a 3D model, and uniformly sampling the surfaced model to generate a uniformly sampled point cloud.

The method may comprise:
identifying a closest point in the point cloud to each point in the uniformly sampled point cloud, and flagging the point in the uniformly sampled point cloud as below the predetermined detail level if a distance between the point in the uniformly sampled point cloud and the identified closest point exceeds a threshold distance.

The method may comprise determining an optimal viewing position for each flagged point. The optimal viewing position may be based on an optimal focal distance of the scanning section. The optimal view position may be based on a normal line extending from the flagged point.

The method may comprise verifying each optimal viewing position to determine that the flagged point will not be occluded when viewed from the scanning section. The method may comprise ray-casting.

The method may comprise determining that the optimal viewing position is occluded, and adjusting the optimal viewing position to reach an unoccluded position. The optimal viewing position may be adjusted by adjusting the angle of the normal line. The optimal viewing position may be adjusted by adjusting the position along the normal line. The optimal viewing position may be iteratively adjusted until the unoccluded position is reached.

The method may comprise ranking each optimal viewing position according to the number of flagged points visible therefrom.

The method of the second aspect may be carried out iteratively. Accordingly, the point cloud of the dental object may be a point cloud obtained by a previous iteration of the method.

The point cloud of the dental object may be an initial point cloud and may be obtained by a pre-programmed scan sequence.

According to a third aspect of the disclosure there is provided a three-dimensional scanning method comprising:
identifying a region for replacement in a first point cloud of a dental object; and
patching the region for replacement with a corresponding region from a second point cloud of a dental object.

One of the first point cloud and second point cloud may be a point cloud of a dental impression, and the other of the first point cloud and second point cloud may be a point cloud of a cast from the dental impression.

The method may comprise surfacing the first point cloud, and uniformly sampling the surfaced model to generate a uniformly sampled point cloud.

The method may comprise:
identifying a closest point in the first point cloud to each point in the uniformly sampled point cloud, and
flagging the point in the uniformly sampled point cloud for replacement if a distance between the point in the uniformly sampled point cloud and the identified closest point exceeds a threshold distance.

The method may comprise inverting the second point cloud and aligning it with the first point cloud.

The method may comprise determining a closest point in the uniformly sampled point cloud for each point in the inverted and aligned point cloud of the impression point cloud. The method may comprise, in response to the determined closest point being a point flagged for replacement, adding the point to a temporary point cloud.

The method may comprise editing the temporary point cloud to include neighbouring points of the second point cloud.

The method may comprise clustering the temporary point cloud to form a plurality of patches. The method may comprise aligning each patch to the first point cloud.

The method of the third aspect may be executable by the three-dimensional (3D) dental scanning system of the first aspect.

According to a fourth aspect of the invention, there is provided a computer-readable storage medium comprising instructions, which when executed by a computer, cause the computer to carry out any of the methods defined herein. The computer-readable storage medium may be tangible and/or non-transient.

According to a fifth aspect of the invention, there is provided a computer program product comprising instructions, which when the program is executed by a computer, cause the computer to carry out any of the methods defined herein.

The invention also extends to a computer device having a memory and a processor configured to perform any of the methods disclosed herein.

BRIEF DESCRIPTION OF DRAWINGS

For a better understanding of the invention, and to show how examples of the same may be carried into effect, reference will now be made, by way of example only, to the accompanying diagrammatic drawings in which.

Figure 1:
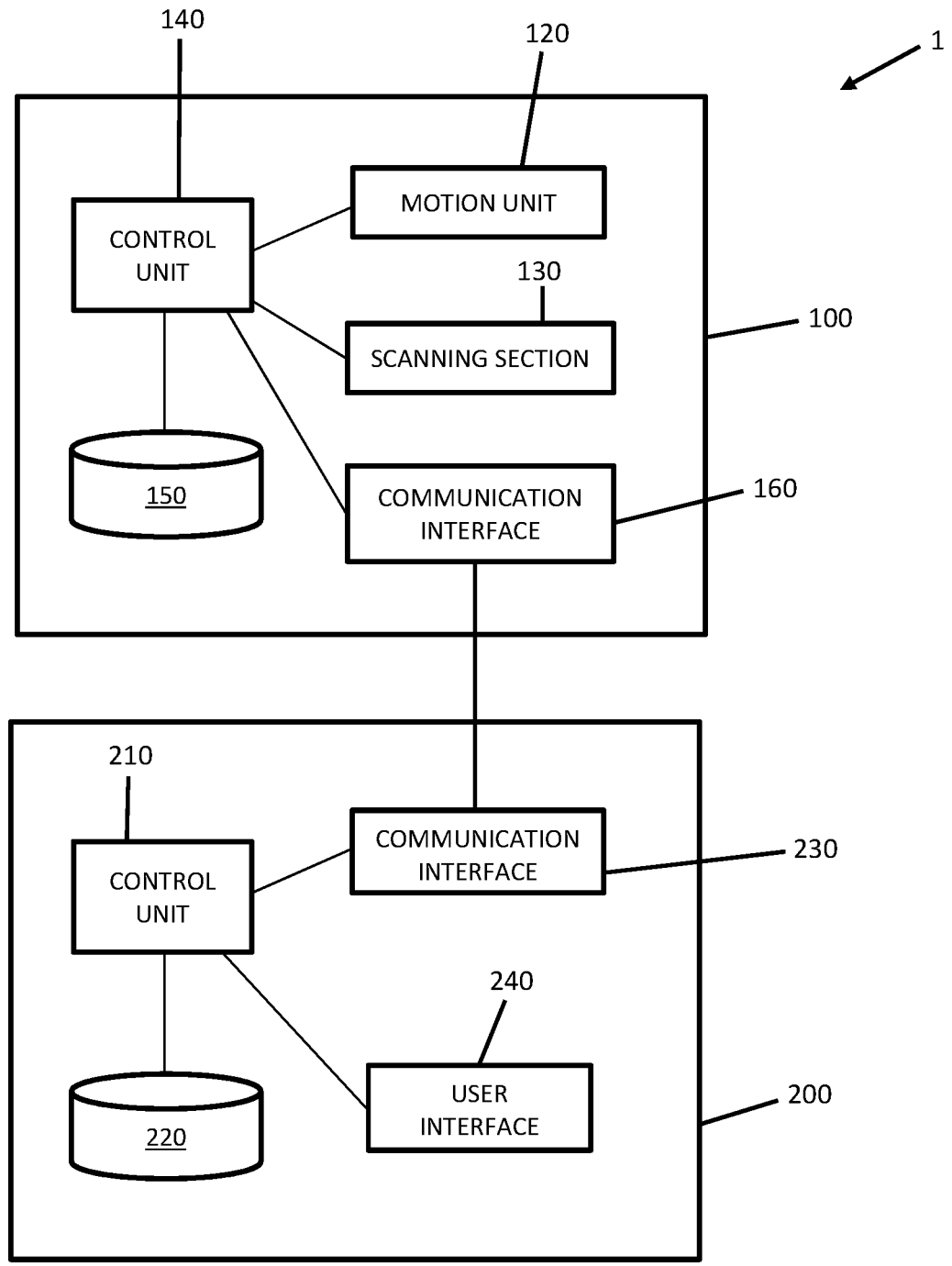
FIG. 1 is a schematic block diagram of an example 3D dental scanning system.
Figure 2:
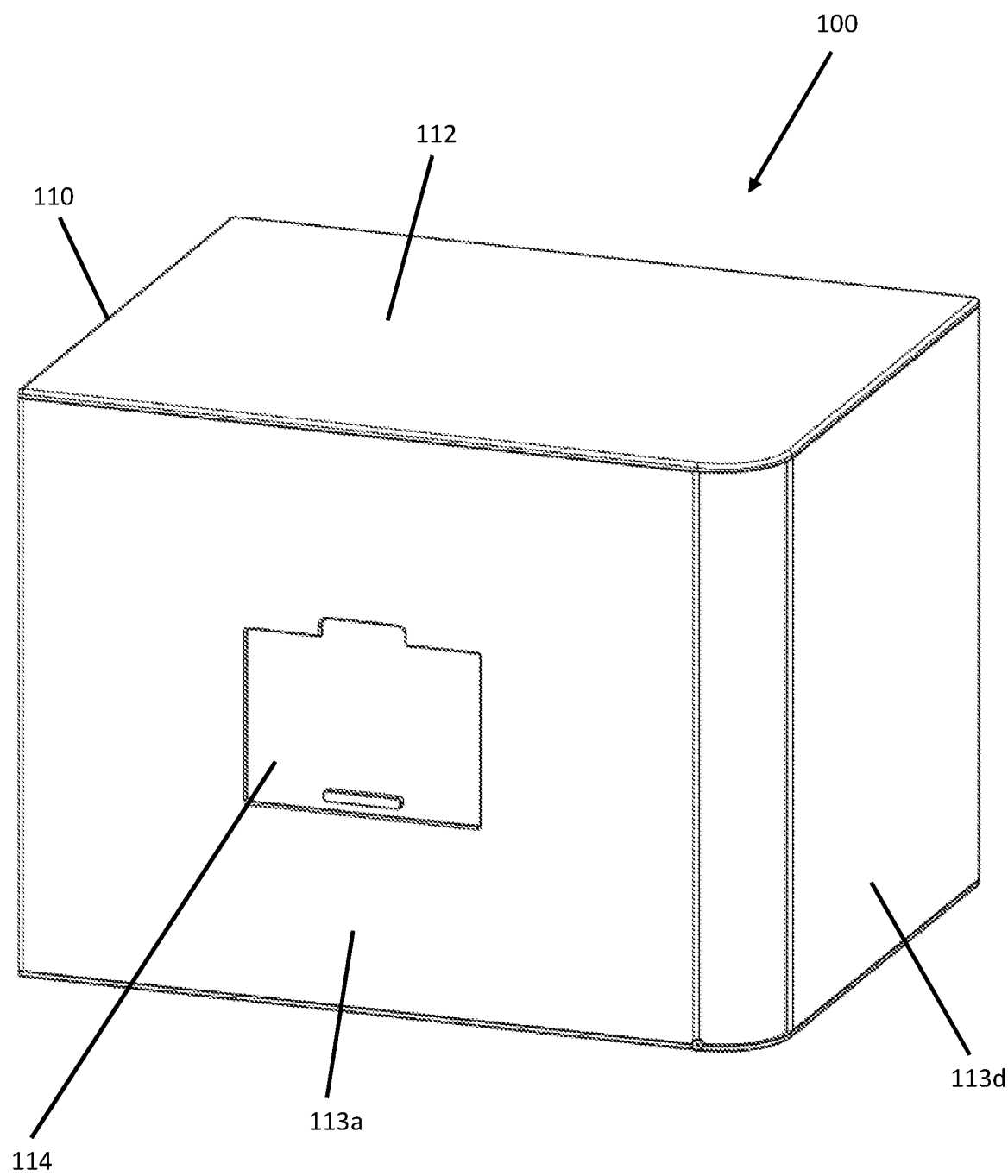
FIG. 2 is a perspective view of an example scanning apparatus of the 3D dental scanner.

In the drawings, corresponding reference characters indicate corresponding components. The skilled person will appreciate that elements in the figures are illustrated for simplicity and clarity and have not necessarily been drawn to scale. For example, the dimensions of some of the elements in the figures may be exaggerated relative to other elements to help to improve understanding of various example examples. Also, common but well-understood elements that are useful or necessary in a commercially feasible example are often not depicted in order to facilitate a less obstructed view of these various example examples.

DESCRIPTION

In overview, examples of the disclosure provide a 3D dental scanner for scanning a dental object, wherein the scanner provides 5 axes of relative motion between the dental object and the scanning section, whilst retaining the dental object in a substantially horizontal plane. As a result, no clamps, jigs or other securing mechanisms are required to secure the dental object in place. This enables the accurate scanning of dental objects that would otherwise deform when clamped, such as dental impressions.

FIG. 1-6 show a 3D dental scanning system 1 in accordance with an example of the disclosure. The dental scanning system 1 comprises a scanning apparatus 100 and a controlling device 200.

The scanning apparatus 100 is shown in detail in FIG. 2-5. The scanning apparatus 100 comprises an enclosure 110, which retains and supports the other components of the scanning apparatus 100. In the example shown, the enclosure 110 takes the form of a substantially cuboid housing, having a bottom wall 111, top wall 112 and four substantially vertical sidewalls 113a-d. A front wall 113a of the sidewalls 113 comprises a door 114 to access the interior of the enclosure 110. For example, the door 114 may be a sliding door.

The dimensions of the enclosure 110 may be approximately 440 mm in height between bottom wall 111 and top wall 112, approximately 580 mm between walls 113b and 113d, and approximately 450 mm between walls 113a and 113c. These dimensions allow the scanning apparatus 100 to be placed on a desktop or work surface, for example in a dental surgery.

Figure 3:
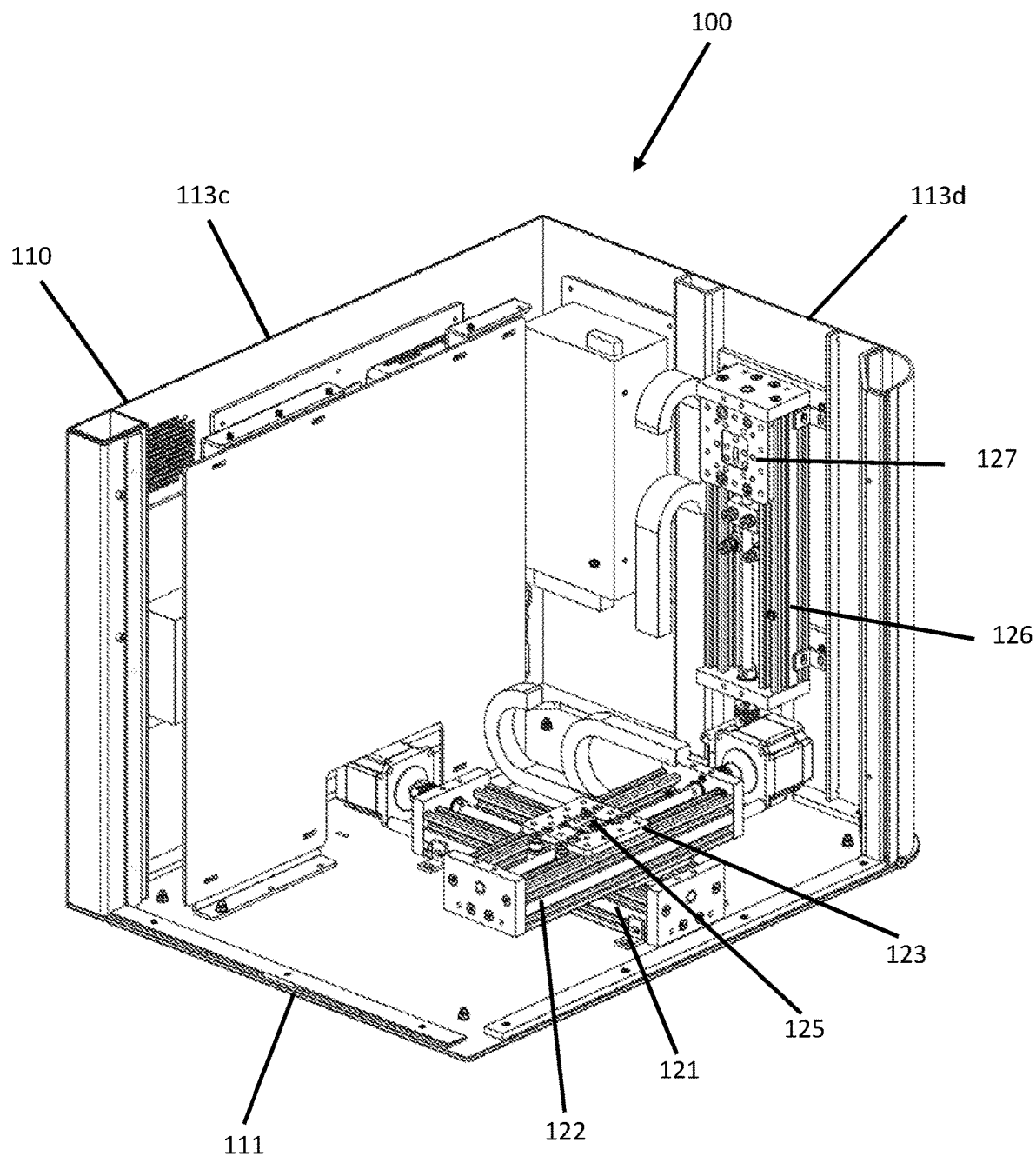
FIG. 3 is a perspective view of the example scanning apparatus of FIG. 2 with parts of the enclosure removed to reveal the interior of the scanner.
Figure 4:
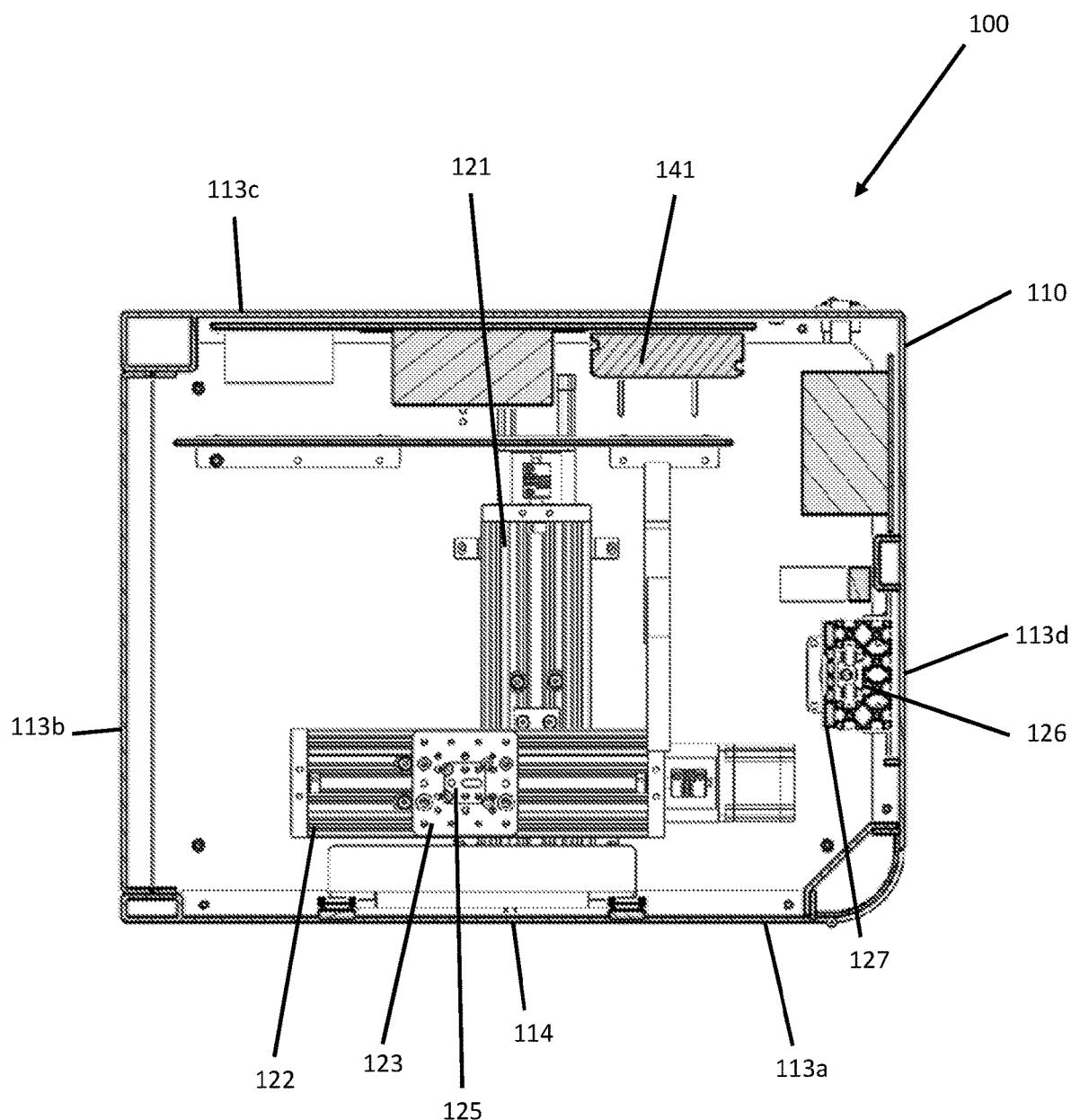
FIG. 4 is a plan cross-section view of the example scanning apparatus of FIG. 2-3.
Figure 5:
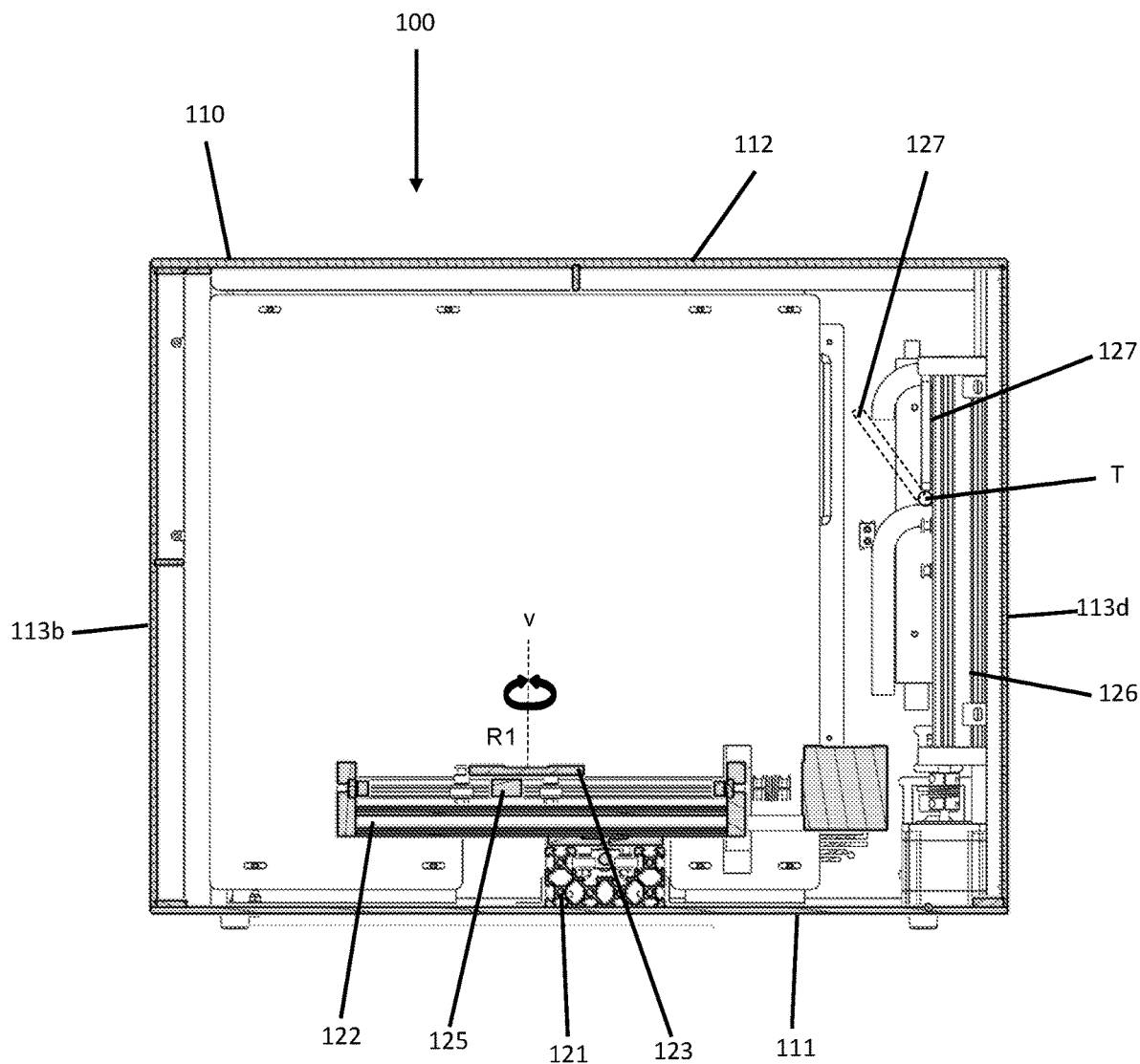
FIG. 5 is a side cross-section view of the example scanning apparatus of FIG. 2-4.
Figure 6:
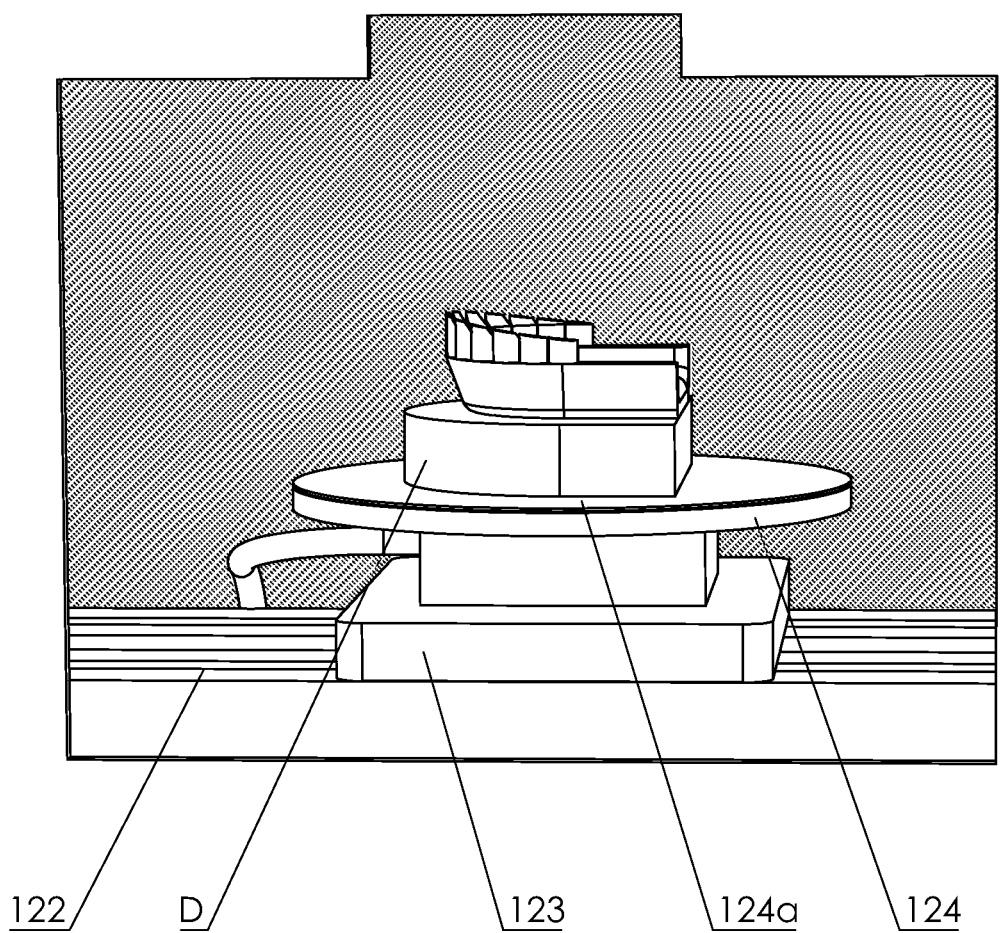
FIG. 6 is a side view through the door of the example scanning apparatus in use.

Turning now to FIG. 3-5, the scanning apparatus 100 comprises a motion section 120. The motion section 120 may comprise a plurality of actuators.

The motion section 120 comprises a first linear actuator 121. The first linear actuator 121 is mounted on the bottom wall 111, and is configured for motion in a first horizontal direction, hereinafter referred to as the X direction.

The motion section 120 also comprises a second linear actuator 122, which is mounted on the first linear actuator 121. Accordingly, the first linear actuator 121 is configured to translate the second linear actuator 122 in the X direction.

A plate support element 123 is mounted on the second linear actuator 122. The plate support element 123 is configured to support a plate 124, which can be best seen in FIG. 6. The plate 124 defines a scanning surface 124a upon which a dental object D can be placed. The plate 124 may take the form of a substantially planar surface, which is circular in plan view and which is disposed in a substantially horizontal plane.

In one example, the scanning surface 124a comprises a high-friction surface. For example, a non-slip mat may be disposed on the scanning surface 124a. The high-friction surface may for example comprise ridges, bumps or other projections that increase the friction between the surface 124a and the dental object D placed thereon. Accordingly, the dental object D remains in position on the scanning surface 124a during motion of the surface 124.

The second linear actuator 122 is configured to move the plate support element 123, and thus the plate 124, in a second horizontal direction. The second horizontal direction is perpendicular to the first horizontal direction, and is hereinafter referred to as the Y direction. Accordingly, the first linear actuator 121 and second linear actuator 122 act together to translate the plate support element 123 and plate 124 horizontally in the X and Y directions.

In addition, the motion section 120 comprises a rotary actuator 125. The rotary actuator 125 is configured to rotate the plate 124 about a vertical axis V in a rotation direction R1. The axis may for example pass through the centre of the scanning surface 124a.

The motion section 120 furthermore comprises a third linear actuator 126. The third linear actuator 126 is mounted vertically, for example on the interior of sidewall 113d. The third linear actuator 126 comprises a scanning section mounting portion 127, to which a scanning section 130 may be mounted. The scanning section 130 is discussed in more detail hereinbelow. The third linear actuator 126 is configured to move the scanning section mounting portion 127 in a vertical direction, substantially perpendicular to the X and Y directions. The vertical direction may be hereinafter referred to as the Z direction.

The third linear actuator 126 is configured to move the scanning section mounting portion 127 to a position in which the scanning section 130 is in substantially the same horizontal plane as the dental object D. For example, the lower end of the third linear actuator 126 may terminate in approximately the same horizontal plane as the plane of the plate 124, or below the plane of the plate 124. This may enable the scanning section 130 to scan in a substantially horizontal direction, thereby accurately capturing the side aspects of the dental object D.

In addition, the motion section 120 comprises a tilt actuator (not shown) which is configured to tilt the scanning section mounting portion 127. Accordingly, the tilt actuator is configured to alter the pitch of the scanning section 130. In particular, as shown in FIG. 5 in dotted lines, the scanning section mounting portion 127 may be moved between a first position and a second position. In the first position, the scanning section mounting portion 127 is disposed in a vertical plane substantially parallel to the plane of the third linear actuator 126. In the second position, the top of the scanning section mounting portion 127 is rotated away from the plane of the third linear actuator 126 in rotation direction R2. The scanning section mounting portion 127 is therefore configured to tilt about a horizontal tilt axis T. In one example, the tilt axis T passes through the bottom of the scanning section mounting portion 127.

Accordingly, the plate 124 and scanning section 130 are configured for relative movement in five axes of motion: translation in the X, Y and Z directions, rotation of the plate 124 and tilt of the scanning section 130.

In addition, the plate 124 and scanning section 130 may be configured for independent relative movement. In other words, each actuator may be independently actuated. Accordingly, the plate 124 and scanning section 130 are not retained in a fixed relationship, such as a relationship in which the centre of the plate 124 (and thus the dental object D) is retained in the centre of the view of the scanning section 130. Accordingly, the scanning section 130 having freedom of movement with respect to the centre of the plate 124 allows the scanning section 130 to be moved to positions offset from the centre of the plate 124. This in turn may allow the capture of areas of interest which would not be able to be captured if the scanning section 130 is only able to capture images centred on the centre of the plate 124.

It will be appreciated that the actuators may comprise any suitable mechanism for translating or rotating the plate 124 or scanning section 130. For example, the actuators may comprise a drive screw, a piston jacks or a screw jack. In some examples, the actuators are driven by a motor. In some example, each actuator is driven by a respective motor, thought it will be appreciated that in other examples two or more actuators may be driven by the motor.

Figure 7:
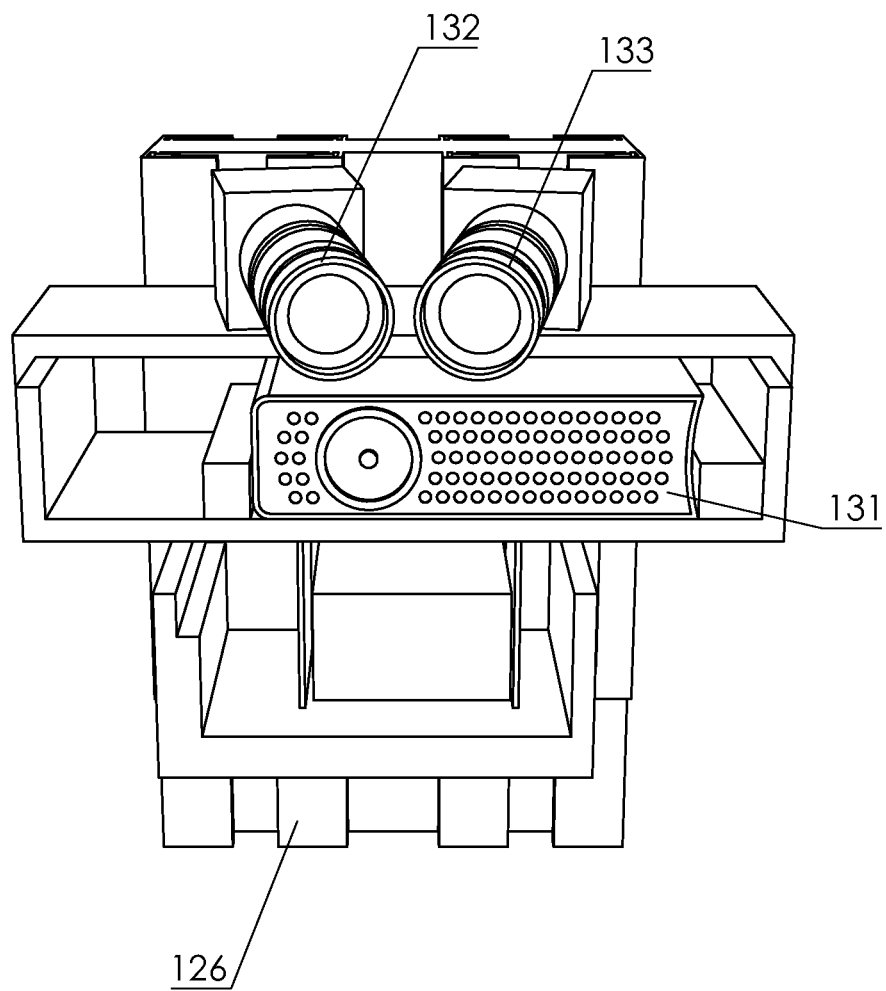
FIG. 7 is a perspective view of a first example scanning section of the example 3D dental scanner of FIG. 1-6.

Turning now to FIG. 7, an example of the scanning section 130 is shown in detail. The scanning section 130 comprises a structured light scanner, comprising a projector 131 and a pair of cameras 132, 133.

The projector 131 is configured to project a structured light pattern onto the dental object D. The cameras 132, 133 are disposed above the projector 131. The cameras 132, 133 are disposed in the same horizontal plane. Each camera 132, 133 is disposed equidistant the projector 131. Accordingly, lenses of the cameras 132, 133 and projector 131 can be connected by a notional inverted triangle with a horizontal top edge. The cameras 132, 133 are angled toward each other, such that their focal points will converge.

Returning to FIG. 1, the scanning apparatus further comprises a control unit 140. The control unit 140 is configured to control the operations of the scanning apparatus 140. For example, the control unit 140 is configured to control the motion unit 120 and the scanning section 130 to obtain a 3D scan of the dental object.

The control unit 140 comprises a compute element, such as a CPU (central processing unit), GPU (graphics processing unit) or FPGA (field programmable gate array).

The scanning apparatus 100 further comprises a storage 150. The storage 150 may store transiently or permanently any data and/or instructions required for the operation of the scanning apparatus 100. The storage may comprise volatile and/or non-volatile memory, including ROM, RAM, EEPROM, solid state drives and hard disk drives.

In one example, the control unit 140 and storage 150 may be comprised in a mini-PC 141. The control unit 140 and storage may also be comprised in a microcontroller (e.g. an Arduino®). For example, the mini-PC 141 may control the scanning section 130, as well as sending control instructions to the microcontroller, which in turn controls motion of the motion section 130.

The scanning apparatus 100 may further comprise a communication interface 160. The communication interface 160 is configured to transmit and receive data and instructions from the controlling device 200. For example, the communication interface 160 comprises a network interface, such as a wired or wireless network interface. In other examples, the communication interface 160 may comprise a serial connection, USB connection or any other suitable data transmission mechanism.

Again returning to FIG. 1, the controlling device 200 comprises a control unit 210, a storage 220, a communication interface 230 and a user interface 240. The control unit 210 comprises a compute element, such as a CPU (central processing unit), GPU (graphics processing unit) or FPGA (field programmable gate array). The storage 220 may store transiently or permanently any data and/or instructions required for the operation of the controlling device 200. The storage may comprise volatile and/or non-volatile memory, including ROM, RAM, EEPROM, solid state drives and hard disk drives.

The communication interface 230 is configured to transmit and receive data and instructions from the scanning apparatus 100. For example, the communication interface 230 comprises a network interface, such as a wired or wireless network interface. In other examples, the communication interface 230 may comprise a serial connection, USB connection or any other suitable data transmission mechanism.

The user interface 240 may take the form of any suitable input and output devices that allow the user to input control instructions to the scanning apparatus 100 and/or view the resulting models derived from the scans. For example, the user interface 240 may comprise one or more of a monitor or other screen, a keyboard, a mouse and a touch screen interface. The controlling device 200 may take the form of a desktop or laptop computer.

In use, the door 114 of the scanning apparatus 100 is opened and a dental object D, such as a cast model or a dental impression, is placed on the plate 124. The scanning routine of the dental object is then initiated, for example by a user making an appropriate user input via user interface 240.

Subsequently, the controller 140 controls the motion section 120 and scanning section 130, so that they move to a desired scanning position, in which a desired portion of the dental object is visible to the scanning section 130 at a desired viewing angle.

The motion section 120 may translate the plate 124 in the X or Y directions by activating the linear actuators 121 or 122. The motion section 120 may also rotate the plate 124 using the rotary actuator 125. Furthermore, the motion section 120 may translate the scanning section 130 in the Z direction using the linear actuator 123, and may tilt the scanning section 130 using the tilt actuator.

Once the motion section 120 has moved the plate 124 and scanning section 130 to the desired scanning position, the projector 131 projects a light pattern onto the dental object, and an image is captured by one or both of the cameras 132, 133.

From the captured image or images, a 3D point cloud is derived, according to a structured light scanning technique. It will be appreciated that part of the process of deriving the 3D point cloud from the captured images may be carried out by the controller 140, with further processing carried out by the controller 210.

The process of controlling the motion section 120 so as to position the dental object D and scanning section 130 to a desired scanning position, may be repeated a plurality of times, so as to capture scans of the model from a plurality of desired scanning positions. The point clouds derived from the different scan positions may be combined to form a point cloud of the dental object D. Example methods of scanning, in which a plurality of scans are captured and combined, are discussed in more detail below with respect to FIGS. 9 and 10.

Accordingly, the motion section 120 and scanning section 130 may be moved relative to each other in 5 axes of motion. This allows the scanning section 130 to capture scans from a very wide range of positions, therefore providing a wide-coverage scan with high detail. Furthermore, the scans can be captured without requiring clamping or other securement of the dental object D to the plate 124.

Figure 8A:
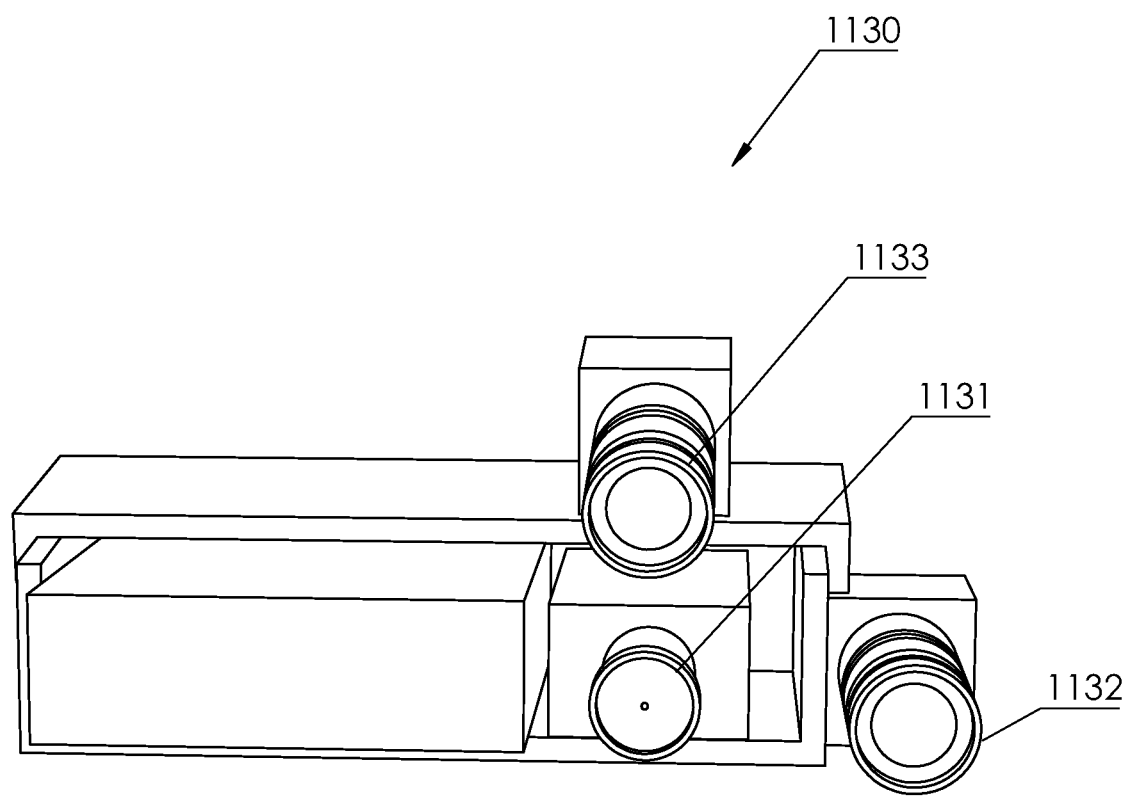
FIGS. 8A and 8B is a perspective view of a second example scanning section of the example 3D dental scanner of FIG. 1-6.
Figure 8B:
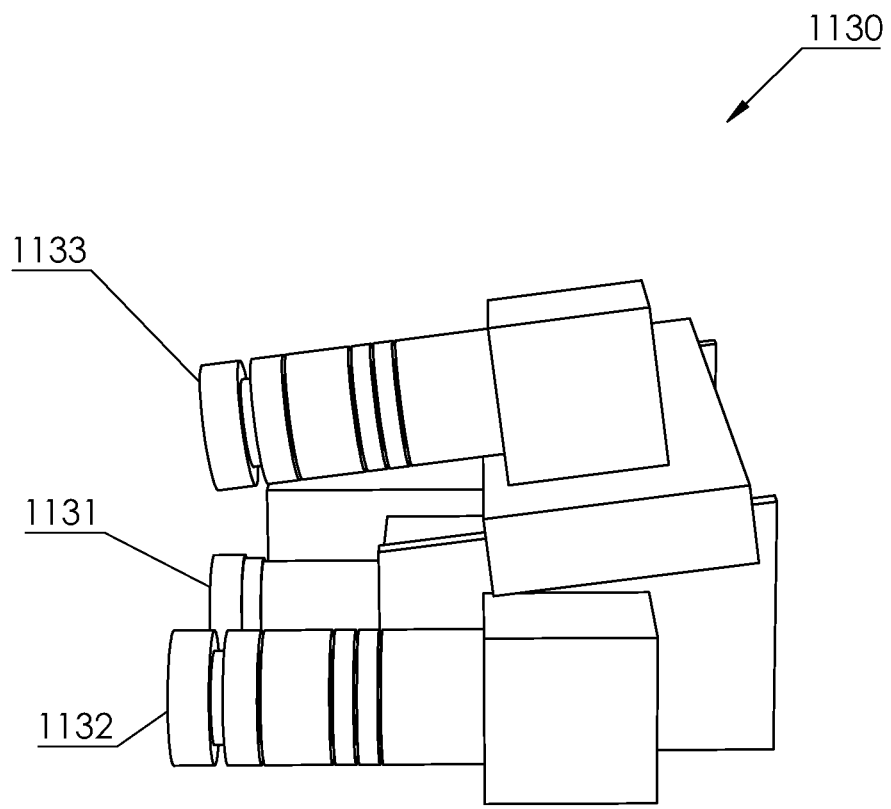

FIGS. 8A and 8B show a second example scanning section 1130. Like the scanning section 130, the scanning section 1130 comprises a projector 1131 and a pair of cameras 1132, 1133. A first of the two cameras 1132 and the projector 1131 are arranged in the same horizontal plane. A second of the two cameras 1133 and the projector 1131 are arranged in the same vertical plane. Accordingly, the lenses of the two cameras 1132, 1133 and the projector 1131 are arranged in a notional "L"-shape.

The scanning section 1130 is configured to operate in a first mode, which may be referred to herein as a horizontal mode, in which camera 1132 and projector 1131 are used in scanning. Accordingly, the first camera 1132 and the projector 1131 form a stereo pair with a horizontal baseline extending therebetween. In the horizontal mode, the projector 1131 may project structured light patterns (e.g. a series of lines) that are orthogonal to the horizontal baseline.

The scanning section 1130 is also configured to operate in a second mode, which may be referred to herein as a vertical mode, in which camera 1133 and projector 1131 are used in scanning. Accordingly, the second camera 1133 and the projector 1131 form a stereo pair with a vertical baseline extending therebetween. In the vertical mode, the projector 1131 may project structured light patterns (e.g. a series of lines) that are orthogonal to the vertical baseline.

The scanning section 1130 is also configured to operate in a third mode, which may be referred to herein as a diagonal mode, in which both first camera 1132 and second camera 1133 are used in scanning. In this mode, the first camera 1132 and second camera 1133 form a stereo pair having a diagonal baseline extending therebetween. The projector 1131 projects structured light patterns that are orthogonal to the diagonal baseline.

In one example, the scanning section 1130 is configured to operate in a trifocal mode. In this mode, rather than making use of a stereo scanning pair having two optic centres, each of the first camera 1132, second camera 1133 and projector 1131 form an optic centre. In the trifocal scanning mode, rather than calculating a fundamental matrix (also known as a bifocal tensor) that is based on two images, a trifocal tensor is computed, expressing the correspondence in points between images captured from all three optic centres. The trifocal tensor may for example be calculated in the manner set out in Richard Hartley and Andrew Zisserman (2003). *"Online Chapter: Trifocal Tensor" (PDF)*. *Multiple View Geometry in computer vision*. Cambridge University Press. ISBN 978-0-521-54051-3, the contents of which are expressly incorporated herein by reference.

In use, the controller 140 controls the scanning section 1130 so as to selectively operate in either the vertical mode or horizontal mode. This allows the scanning apparatus 100 to accurately scan regions of the dental model that would be otherwise be occluded if scanned using the scanning section 130, thereby improving the coverage of the scan and the accuracy of the 3D model.

It will be appreciated that the scanning section 1130 is one example configuration in which a first notional line connecting the first camera 1132 and projector 1131 and a second notional line connecting the second camera 1133 and projector 1131 are non-colinear. In the example scanning section 1130, the first and second notional line are orthogonal, with the first notional line being substantially horizontal. However, in further examples the scanning section may be configured in other ways in which the first and second notional lines are non-colinear. For example, the angle between the lines may be acute or obtuse. Furthermore, the notional lines need not coincide with the horizontal and/or vertical planes.

Figure 9:
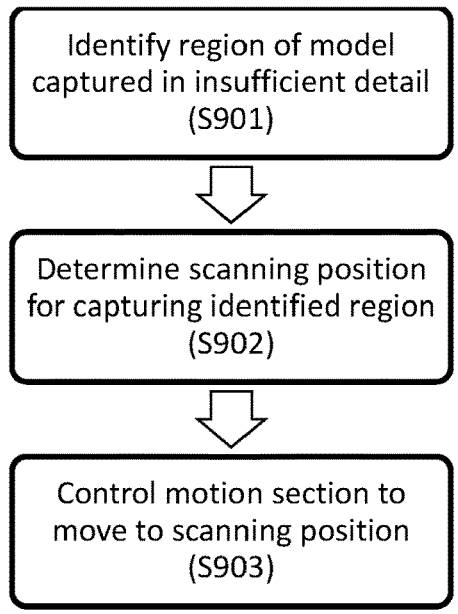
FIG. 9 is a schematic flowchart of a first example scanning method.

FIG. 9 is a flowchart of an example scanning method. The scanning method generates a sequence of scan locations, so as to provide a high-coverage scan of the dental object.

In step S901, an input point cloud of a dental object is analysed, and a region of the object that is scanned at detail level below a predetermined sufficient detail level is identified. In step S902, a scanning position for capturing the identified region is determined. In step S903, the motion section 120 and scanning section 130 are moved to the scanning position to capture the identified region.

Figure 10:
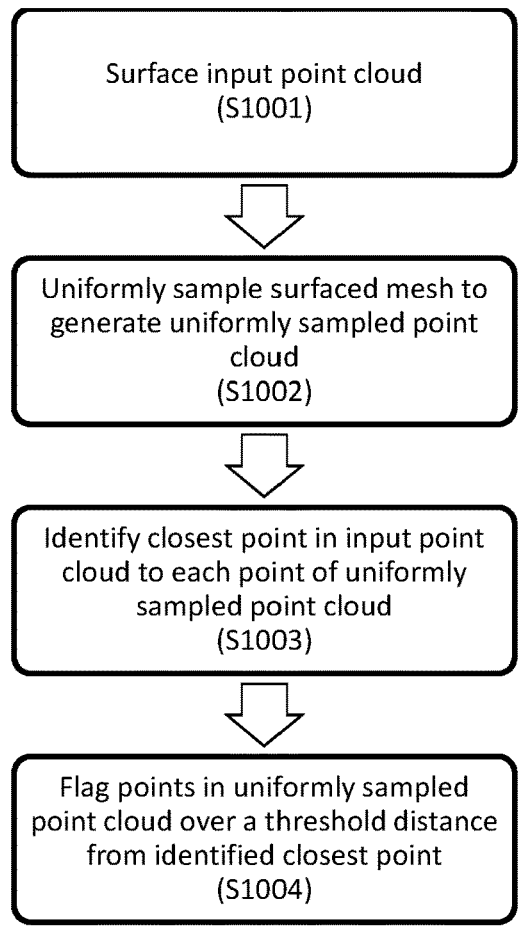
FIG. 10 is a schematic flowchart showing the first example scanning method of FIG. 9 in more detail.

FIG. 10 illustrates the process of step S901 in more detail. In a first step S1001, the input point cloud is surfaced. This is the process of re-constructing the 3D surface of the dental object based on the points in the point cloud. For example, a Poisson surfacing algorithm is used to generate a surface from the 3D model. This results in a surfaced mesh.

Subsequently, in step S1002, the surfaced mesh is sampled at a uniform distance, so as to generate a uniformly sampled point cloud. In one example, the sampling distance is 0.5 mm. The distance may be varied, with smaller distances increasing accuracy at the expense of processing speed.

Subsequently, in step S1003, for each point in the uniformly sampled point cloud, a closest point in the input point cloud is identified.

Subsequently, in step S1004, if the distance between the point in the uniformly sampled point cloud and the identified closest point exceeds a threshold distance, it is indicative that this region of the input point cloud has been captured in insufficient detail. Each point that exceeds the threshold is flagged, for example by altering the colour of the point.

The threshold may for example be 0.3 mm, though in a similar manner to the sampling distance, smaller or larger distances may be employed.

Optionally, if the closest point in the input point cloud is a relatively large distance away (e.g. over 10 mm), the point may then be removed from the uniformly sampled point cloud. Such large distances may be indicative of a region of the uniformly sampled point cloud where the surfacing of the model is inaccurate, and therefore should not be used.

In one example, the dental model may comprise unscannable regions, for example with black or highly reflective parts. The areas of the uniformly sampled point cloud which correspond to an unscannable region will not have proximate corresponding points in the input point cloud. Accordingly, to avoid repeatedly attempting to scan an unscannable region, a list is maintained of every previous scan location from which a scan of the dental object has already been obtained. A ray-cast is run from each of these previous scan locations to see if a previous view should have captured the unseen point already. If the ray-cast indicates that the unseen point was visible from a previous scan location, it may be determined that the point is an unscannable point. In some examples, a point may be determined to be unscannable when there exist a predetermined number of previous views (e.g. 2) that should have captured the point, but did not. This avoids discarding points that are unscannable due to an anomalous reflection in one view only.

Figure 11:
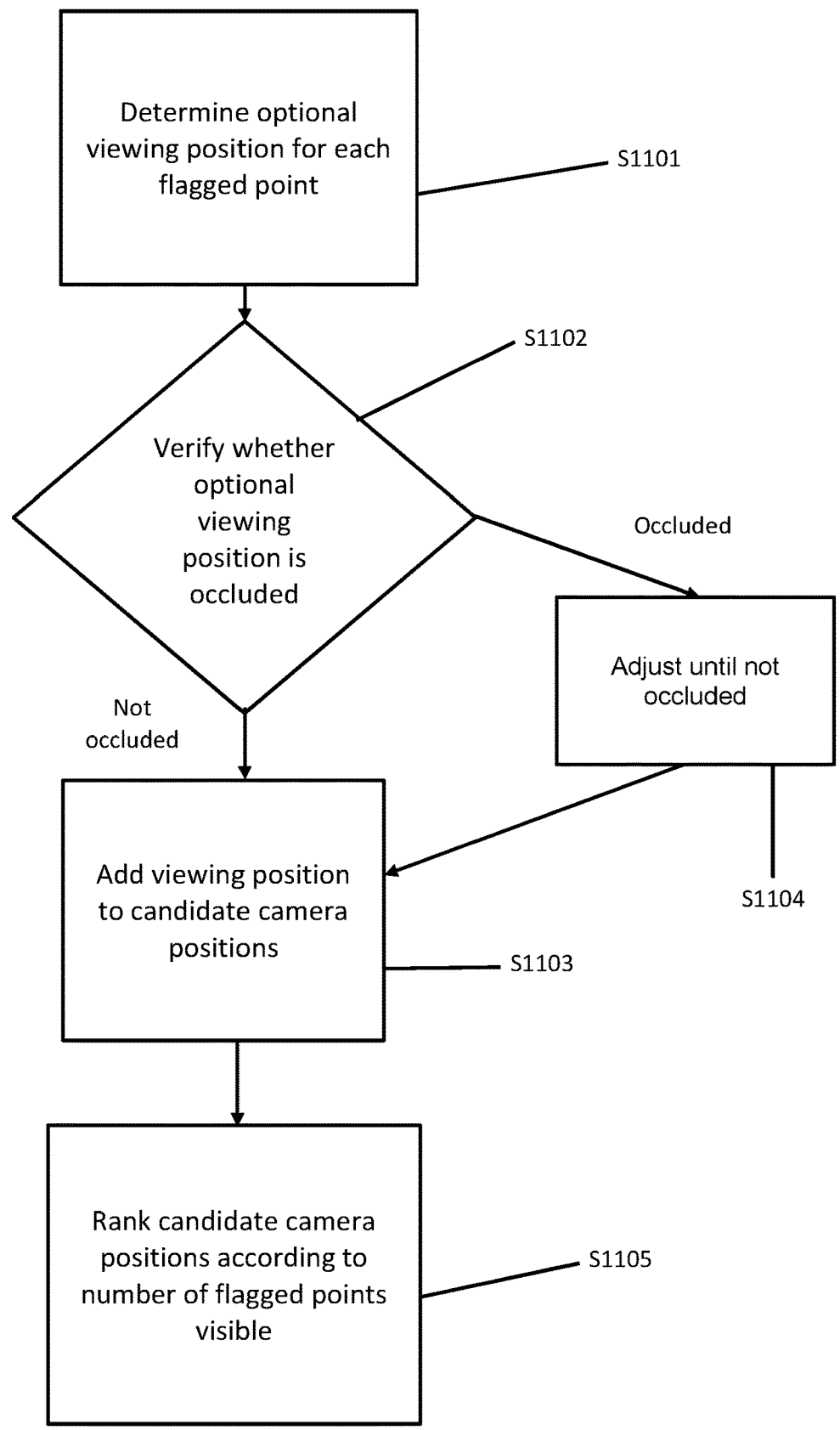
FIG. 11 is a schematic flowchart showing the first example scanning method of FIG. 9 in more detail.

FIG. 11 illustrates the process of step S902 in more detail. In a first step S1101, for a given flagged point, an optimal viewing position is determined. In one example, the optimal viewing point is determined by first projecting a normal line from the flagged point. The normal line is a line perpendicular to a plane tangential to the flagged point. A point on the normal line that is at a distance from the flagged point corresponding to the optimal focal distance of the scanning section 130, 1130 is then determined to be the optimal viewing position for the flagged point.

In a second step S1102, the optimal viewing position is verified to ensure the flagged point will not be occluded when viewed from the cameras of the scanning section 130, 1130. For example, the scanning section is virtually positioned at the optimal viewing position, and a ray-cast is carried out from the virtual position of the centres of the cameras to the flagged point.

If the ray-cast shows that the cameras have clear line-of-sight to the flagged point, this camera position is stored in a list of candidate scanning section positions (S1103).

It will be appreciated that, as discussed above, the scanning section 1130 may operate in one of a plurality of modes, in which one or more cameras and the projector are in operation. Accordingly, in one example, a clear line-of-sight from all of the cameras that are in use in the current scanning mode is required. In further examples, if a clear line-of-sight is available in one of the scanning modes, the camera position is stored, along with a record of the mode in which the clear line-of-sight is available. Accordingly, the scanning method may automatically select the most appropriate scanning mode for capturing a particular point. In some examples, a predetermined ranking may be defined, such that the best available scanning mode is used. For example, the method may select the trifocal or diagonal modes if both cameras and the projector have a clear line-of-sight, with the horizontal and vertical modes acting as fall-backs.

As the projector is active in all of the scanning modes, in one example, the line-of-sight from the projector may be determined before the line-of-sight from either of the cameras. This acts as an efficient first filter, avoiding computing a ray-cast to the cameras in instances where the projector is occluded.

If, on the other hand, there is not a clear line-of-sight, the angle of the normal line is iteratively adjusted. For example, the angle of the normal line is adjusted by 1 degree in one axis at a time, until a position is arrived at in which the line of sight is clear (S1104). Accordingly, a conical pattern is traced, with the point at the peak of the cone and the position of the camera forming the base of the cone. The radius of the base of the cone may be progressively increased, until a position with clear line of sight is found. The method therefore effectively combines a brute-force search with optimisation based on the ideal position.

In another example, in the event that there is not a clear line-of-sight, the position of the camera may be iteratively adjusted along the normal line, so as to be either more or less proximate to the point than the optimal focal distance. This provides another possible means of arriving at a position close to the ideal position with an unobstructed view of the point.

The adjusted position is then stored in the list of candidate scanning section positions (S1103).

In step S1105, the candidate scanning section positions are ranked according to the number of flagged points visible therefrom.

For example, for each candidate position, all flagged points visible from the position are stored. This list of flagged points may then be pruned to remove one or more of the following:
 Points which do not fall within the 2D screen coordinates of all cameras.
 Points whose 3D normal faces away from each camera. A threshold angle, for example of 70 degrees from the camera, may be used to discard the points.
 Points which are too far away from or too close to any of the cameras, based on stored depth of field parameters of the camera.
 Points which are occluded from any camera projection.
The candidate scan positions are then ranked based on the number of flagged points visible.

In one example, if the list of candidate positions exceeds a predetermined threshold size, the candidate positions are randomly sampled to reduce the list size before step S1105 is carried out. Whilst randomly sampling may result in missing certain points, the repeated iteration of the algorithm results in the points being likely to be captured in later iterations. The threshold may for example be 1000.

In one example, the ranking is such that a particular flagged point may not be repeatedly counted once it has appeared in a particular scan. That is to say, a point already appearing in one scan position does not then subsequently contribute to the count of points visible in other lower-ranking scan positions.

In one example, the full list of candidate scan positions may be returned. In other examples, the first n views may be returned. In some examples, a list comprising scan positions corresponding to a predetermined percentage of the flagged points may be returned. The motion section is then moved to the scan positions to scan the identified regions of insufficient detail.

In some examples, the method of FIG. 9 is carried out iteratively. Accordingly, the point cloud obtained as an output of one iteration of the method forms the input point cloud for a subsequent iteration of the method.

In some examples, an initial point cloud may be obtained by a pre-programmed scan sequence. This initial point cloud may then form the input point cloud of the method.

The example method of FIG. 9-11 may be carried out by the scanning system 1. It may for example be carried out by the controlling device 200.

Another example scanning method will now be described with reference to FIG. 12.

As discussed above, dental impressions are a negative imprint of a patient's inter-oral structures, from which a dental model may be cast. Scanning a cast dental model may result in missing crucial areas of detail which may be more readily visible in the dental impression. For example, areas of detail in the interproximal regions and the retracted gingival sulcus around a crown preparation may not be captured accurately. Conversely, regions which may be difficult to accurately scan in a dental impression may be more readily visible in the cast model.

In the example scanning method, a 3D model derived from scanning a dental impression (hereinafter the "impression 3D model") may be combined with a 3D model derived from scanning a dental model cast from the impression (hereinafter the "cast 3D model"). However, due to differences between the cast 3D model and impression 3D model, for example caused by the process of pouring the model, the cast 3D model and impression 3D model, it may be inaccurate to simply invert the impression 3D model and combine it with the cast 3D model.

The example method comprises a step S1201, in which defective regions are detected in a 3D model derived from scanning a dental model cast from a dental impression.

In one example, the defective regions are detected in a similar manner to the detection of regions scanned in insufficient detail in step S901 above. For example, the point cloud of the cast 3D model may be surfaced, and then uniformly sampled to produce a uniformly sampled point cloud. Points in the uniformly sampled point cloud that are above a threshold distance from the nearest point in the cast 3D model point cloud are flagged as defective. In this example a smaller threshold may be used, on the basis that it is unlikely that there will be large regions of the model missing as may be the case during the scanning process. For example, the threshold may be 0.1 mm.

In a further example, an edge detection technique may be used to identify holes in the point cloud of the cast 3D model.

The example method comprises a step S1202, in which the defective regions are patched a corresponding region from a 3D model of a dental object derived from scanning the dental impression.

Figure 13:
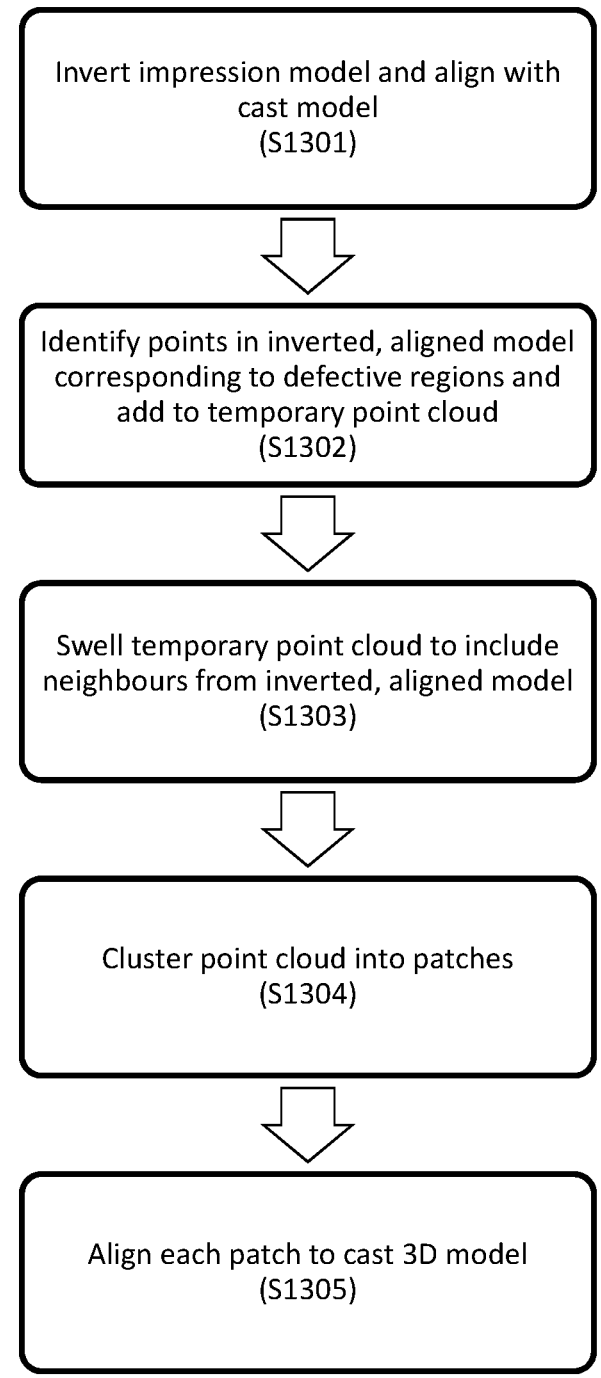
FIG. 13 is a schematic flowchart showing the second example scanning method of FIG. 12 in more detail.

FIG. 13 illustrates step S1202 in more detail.

In a first step S1301, the normals of the impression 3D model are inverted and it is aligned to the cast 3D model, using a global registration algorithm.

In a second step S1302, for each point in the inverted and aligned point cloud of the impression 3D model, a closest point in the uniformly sampled point cloud is identified. If the closest point in the uniformly sampled point cloud is flagged as defective, the point in the inverted and aligned point cloud of the impression 3D model is added to a new, temporary point cloud. This temporary point cloud is therefore populated with all points in the inverted and aligned point cloud of the impression 3D model that correspond to defective regions of the cast 3D model.

In the next step S1303, the temporary point cloud is swollen to include neighbouring points of the impression 3D model. Each point in the inverted and aligned point cloud of the impression 3D model that has a nearest neighbour in the temporary point cloud less than a predetermined distance away (e.g. 0.5 mm) is also added to the temporary point cloud.

In the next step S1304, the temporary point cloud is clustered into a plurality of smaller point clouds. This may be based on a nearest neighbour search, with an example search criteria of 0.3 mm. It will be appreciated that other clustering algorithms may be applied to divide the temporary point cloud. The resulting plurality of smaller point clouds each form a patch to be applied to the cast 3D model.

In the next step S1305, each patch is aligned to the cast 3D model, and incorporated thereinto. For example, an alignment algorithm such as the iterative closest point algorithm may be employed.

Figure 12:
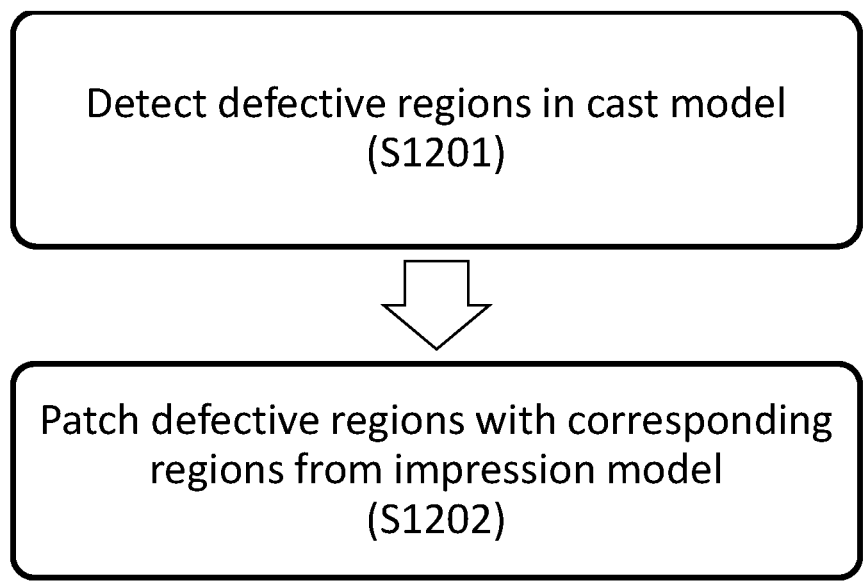
FIG. 12 is a schematic flowchart of a second example scanning method.

It will be understood that the method of FIGS. 12 and 13 can equally be carried out by patching the impression 3D model with the cast 3D model if desired.

In further examples, the method of FIGS. 12 and 13 may be applied to combine two scans of various dental objects.

In one example, the method may be used to combine two impression scans, wherein the impressions are of the same patient. For example, a dentist in practice may take a second impression, wherein it is apparent that a first impression has captured a particular region of the teeth in insufficient detail.

In another example, the method may be applied to combine two scans of cast models. For example, a dental laboratory may take a first scan be taken of the cast model. Subsequently, the cast model may be worked on by the laboratory, for example to fit a prosthesis thereto. In the process of preparing the prosthesis, the cast model may be handled and minor damage may occur to regions of the model, particularly those regions not proximate the prosthesis. Therefore, it may be desirable to combine the first scan of the cast model with a subsequent scan, wherein the method patches the first scan with a second scan of the cast model including the prosthesis.

In some examples, a region of a model may be marked as a donor region, which should act as the area to be patched into the other model, by a user. For example, the region may be selected via user interface 240. Areas of the model not corresponding to the donor region, or not within a predetermined distance of the donor region, may be cropped from the model before applying the method outlined above.

The example method of FIG. 9-11 may be carried out by the scanning system 1. It may for example be carried out by the controlling device 200.

Various modifications or alterations may be made to the examples described herein. For example, it will be appreciated that the functionality of the controller of the scanning apparatus 100 and controlling device 200 may be interchanged. In other words, in some examples functionality described herein as carried out by control unit 140 may be carried out by control unit 210, and vice versa. In some examples, the functionality of the control device 200 may be integrated into the scanning apparatus 100, so that the control device is not necessary. It will be understood that the shape and construction of the enclosure 110 may be varied.

The scanning system and methods described herein advantageously permits accurate scanning from a wide range of viewpoints of pliable materials such as dental impressions, without clamping the impressions which may cause distortion thereof. Furthermore, the construction of the scanning system is such that it can readily be installed in a dental surgery.

In addition, the scanning methods described herein may automatically derive high quality models of dental objects with minimal intervention from an operator of the scanning system. Accordingly, the scanning system may be easily operated with minimal training, for example by a dental nurse or dentist in a surgery. The fact that the scanner can be used with minimal training and on dental impressions may obviate the need to send dental impressions by post to a dental lab. Accordingly, an accurate model of the patient's teeth may be rapidly created.

At least some of the examples described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some examples, the described elements may be configured to reside on a tangible, persistent, addressable storage medium and may be configured to execute on one or more processors. These functional elements may in some examples include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example examples have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example may be combined with features of any other example, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A three-dimensional (3D) dental scanning system for scanning a dental object, comprising:
    a scanning surface configured to support the dental object;
    a scanning section configured to capture a 3D scan of the dental object;
    a motion section configured to move the scanning surface and scanning section relative to each other in five axes of motion, whilst retaining the scanning surface in a substantially horizontal plane, and
    a control unit configured to control the motion section and the scanning section to obtain a 3D scan of the dental object;
    wherein the control unit is configured to:
        a) identify a region of a point cloud of the dental object captured at a level of detail below a predetermined detail level;
        b) identify a scanning position for capturing the identified region; and
        c) control the motion section to move the scanning surface and scanning section to scan the identified region.

2. The system of claim 1, wherein the control unit is configured to:
    surface the point cloud to produce a 3D model;
    uniformly sample the surfaced model to generate a uniformly sampled point cloud;
    identify a closest point in the point cloud to each point in the uniformly sampled point cloud, and
    flag the point in the uniformly sampled point cloud as below the predetermined detail level in response to a distance between the point in the uniformly sampled point cloud and the identified closest point exceeding a threshold distance,
    wherein the control unit is configured to determine an optimal viewing position for each flagged point.

3. The system of claim 2, wherein the control unit is configured to verify each optimal viewing position to determine that the flagged point will not be occluded when viewed from the scanning section, wherein the control unit is configured to determine that the optimal viewing position is occluded, and adjust the optimal viewing position to reach an unoccluded position, and wherein the control unit is configured to rank each optimal viewing position according to the number of flagged points visible therefrom.

4. The system of claim 1, wherein the point cloud of the dental object is a point cloud obtained by a previous iteration of steps (a)-(c).

5. The system of claim 1, wherein the point cloud of the dental object is a point cloud obtained by a pre-programmed scan sequence.

6. The system of claim 1, wherein the five axes of motion comprise:
    translation in a first horizontal direction;
    translation in a second horizontal direction perpendicular to the first horizontal direction;
    translation in a vertical direction;
    rotation of the scanning surface; and
    tilt of the scanning section, and
    wherein the scanning section is movable to a position in the vertical direction that is in substantially the same, or lower, horizontal plane as the dental object and/or scanning surface.

7. The system of claim 1, wherein the scanning section comprises:
    a projector configured to project a structured light pattern onto the dental object, and a camera.

8. The system of claim 7, comprising two cameras disposed on the same plane.

9. The system of claim 7, comprising two cameras, wherein:
    a first of the two cameras and the projector are connected by a first notional line;
    a second of the two cameras and the projector are connected by a second notional line,
    wherein the first notional line and second notional line are non-colinear,
    wherein the scanning section is selectively operable in at least two of:
    a first mode in which the first camera and the projector are activated,
    a second mode in which the second camera and the projector are activated, and
    a third mode in which the first camera, the second camera and the projector are activated.

10. The system of claim 9, wherein the scanning section is operable in a trifocal mode in which the first camera, the second camera and the projector are activated, and each of the first camera, the second camera and the projector form an optic centre.

11. The system of claim 1, wherein the scanning surface is a substantially planar surface.

12. The system of claim 1, wherein the scanning system does not comprise securing means for securing the dental object to the scanning surface.

13. The system of claim 1, wherein the motion section is configured to permit freedom of movement of the scanning section with respect to a centre of the scanning surface.

14. A three-dimensional (3D) scanning method comprising using the 3D dental scanning system of claim 1 to capture a 3D scan of a dental object.

* * * * *